United States Patent [19]

Antelman

[11] Patent Number: 5,571,520
[45] Date of Patent: Nov. 5, 1996

[54] MOLECULAR CRYSTAL REDOX DEVICE FOR PHARMACEUTICALS

[75] Inventor: Marvin S. Antelman, Rehovot, Israel

[73] Assignee: Antelman Technologies Ltd., Providence, R.I.

[21] Appl. No.: 286,007

[22] Filed: Aug. 4, 1994

Related U.S. Application Data

[60] Continuation of Ser. No. 971,933, Nov. 5, 1992, Pat. No. 5,336,499, which is a division of Ser. No. 820,282, Jan. 10, 1992, abandoned.

[51] Int. Cl.$^6$ .................................................. A61K 33/38
[52] U.S. Cl. .......................... 424/405; 424/618; 423/604; 514/495
[58] Field of Search .................... 424/400, 618, 424/405; 514/495; 423/604

[56] References Cited

U.S. PATENT DOCUMENTS

| | | | |
|---|---|---|---|
| 4,055,655 | 10/1977 | Maurer et al. | 514/495 |
| 4,695,353 | 9/1987 | Jansen et al. | 423/604 |
| 4,717,562 | 1/1988 | Jansen et al. | 423/604 |
| 4,784,991 | 11/1988 | Nimrod et al. | 514/495 |
| 4,835,077 | 5/1989 | Megahed et al. | 423/604 |
| 4,915,955 | 4/1990 | Gömöri | 424/618 |
| 4,952,411 | 8/1990 | Fox, Jr. et al. | 424/618 |
| 5,017,295 | 5/1991 | Antelman | 210/764 |
| 5,073,382 | 12/1991 | Antelman | 210/764 |
| 5,078,902 | 1/1992 | Antelman | 210/764 |
| 5,089,248 | 2/1992 | Akhtar | 423/604 |
| 5,089,275 | 2/1992 | Antelman | 424/602 |
| 5,098,582 | 3/1992 | Antelman | 210/759 |
| 5,211,855 | 5/1993 | Antelman | 424/618 |
| 5,223,149 | 6/1993 | Antelman | 424/618 |
| 5,336,508 | 8/1994 | Marty | 424/618 |
| 5,362,735 | 11/1994 | Luengo | 514/291 |
| 5,444,052 | 8/1995 | Pieringer et al. | 514/738 |

*Primary Examiner*—Amy Hulina
*Attorney, Agent, or Firm*—Salter & Michaelson

[57] ABSTRACT

The employment of molecular crystals as bactericidal, viricidal and algicidal devices, and specifically the molecular semiconductor crystal tetrasilver tetroxide $Ag_4O_4$ which has two trivalent and two monovalent silver atoms per molecule, and which through this structural configuration generates electronic activity on a molecular scale capable of killing algae and bacteria via the same mechanism as macroscale electron generators.

3 Claims, No Drawings

MOLECULAR CRYSTAL REDOX DEVICE FOR PHARMACEUTICALS

This application is a continuation of my U.S. application Ser. No. 07/971,933 filed Nov. 5, 1992, now U.S. Pat. No. 5,336,499, which was a division of U.S. application Ser. No. 07/820,282, filed Jan. 10, 1982, now abandoned.

BACKGROUND OF THE INVENTION

The present invention relates to the employment of molecular crystals as bactericidal, viricidal and algicidal devices, but more particularly to the molecular semiconductor crystal tetrasilver tetroxide $Ag_4O_4$ which has two trivalent and two monovalent silver atoms per molecule, and which through this structural configuration enables electronic activity on a molecular scale capable of killing algae and bacteria via the same mechanism as macroscale electron generators.

The molecular device of this invention is a multivalent silver diamagnetic semiconductor as previously described in my aforesaid pending U.S. application Ser. No. 07/971,933, now U.S. Pat. No. 5,336,499.

OBJECTS OF THE INVENTION

The main object of this invention is to provide a molecular scale redox device of a single tetrasilver tetroxide semiconductor crystal capable of killing viruses, bacteria, fungi and algae when operating in conjunction with other such devices.

Another object of the invention is to provide a molecular device which can be utilized in pharmaceuticals formulated to destroy pathogens.

Other objects and features of the present invention will become apparent to those skilled in the art when the present invention is considered in view of the accompanying examples. It should, of course, be recognized that the accompanying examples illustrate preferred embodiments of the present invention and are not intended as a means of defining the limits and scope of the present invention.

SUMMARY OF THE INVENTION

This invention relates to a molecular scale device capable of destroying gram positive and gram negative bacteria as well as fungi, viruses and algae. Said molecular scale device consists of a single crystal of tetrasilver tetroxide. Several hundred thousand trillion of these devices may be employed in concert for their bactericidal, fungicidal, and algicidal properties and in various pharmaceutical formulations and therapies. The physical chemistry of said tetroxide devices has already been described in my aforesaid pending application Ser. No. 07/971,933, now U.S. Pat. No. 5,336,499 and is incorporated herein by reference.

DESCRIPTION OF THE INVENTION

The crystal lattice of the $Ag_4O_4$ device operates by transferring electrons from its two monovalent silver ions to the two trivalent silver ions in the crystal in aqueous media in which it is immersed, and which conducts electrons, contributing to the death of pathogens by traversing the cell membrane surface of the pathogens being "electrocuted", not only by these electrons but also by others emanating from other molecular devices in the vicinity of the pathogen. The device is attracted to the cell membrane surface by powerful covalent bonding forces caused by the well-known affinity of silver to certain elements present in the membrane, such as sulfur and nitrogen.

The electron transfer can be depicted by the following redox half reactions in which the monovalent silver ion loses an electron and the trivalent silver gains one as follows:

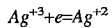

The molecular crystal then will become stabilized with each silver ion having a divalent charge.

Stringent testing was performed in which cultures were actually placed in trypticase soy nutrient broth, which allowed the pathogens being tested to replicate without being detached from its own food supply. Under these conditions the devices were able to kill two strains of *E. coli* at 2.5 PPM; *Micrococcus luteus* at 1.25 PPM; *Staphylococcus aureus* at 2.5 PPM; *Staphylococcus epidermidis* at 0.6 PPM; *Pseudomonas aeruginosa* at 1.25 PPM; and *Streptococcus pyogenes* at 2.5 PPM.

The devices were then evaluated in analogous nutrient used for yeasts, algae and molds utilizing Sabouraud dextrose broth. The infectious yeast pathogen *Candida albicans* was totally killed at 2.5 PPM and that of the Saccharomycetpideae variety at 1.25 PPM. These were also evaluated successfully in mice against murine aids, and in humans against *Candida albicans* both as a douche and intravenously. The devices also were successful externally in humans against *Staphylcoccus epidermidis*, nail fungus and athlete's foot. Intravenous injections completely cured subjects who were suffering from acute diarrhea of ameobic dysentery.

It was found that oxidizing agents, particularly persulfates, enhance the efficacy of said devices.

EXAMPLE 1

The molecular crystal devices were tested as to whether they could kill pathogenic microorganisms with the intent of utilizing them in pharmaceutical applications. Once it could be determined that the devices inhibited a particular microorganism, the minimal concentration required of the $Ag_4O_4$ molecular crystal devices was determined to inhibit the microorganism in nutrient broth. One family of pathogens that are known for their deleterious effects on humans are popularly called "staph" infections. These infections are commonly contracted in hospitals having lax infectious screening procedures. Accordingly, three staph strains were selected as follows for evaluation: *Staphylococcus aureus* 9027, 27543 and *Staphylococcus epidermidis* 12228. The inoculum nutrient broth was prepared according to AOAC specifications so as to contain 0.6–1 million organisms per drop of inoculum, each drop being equal to 0.05 ml. The broth itself was trypticase soy broth BBL 11766 prepared according to label instructions. Accordingly, the broth was prestandardized for the microorganisms in question in order to assure that the number of organisms remained constant within the margins of statistical allowance during the test period. Having carried out the procedures with 0.05 ml. of inoculum and having incubated the organisms for 24 hours at 34°–35° C., it was found that staph organism 9027 was inhibited at 2.5 PPM; number 27543 at 5.0 PPM; and the 2228 organism at 0.625 PPM all in the presence of 10 PPM sodium persulfate. This data was utilized to formulate a dermatological cream which would contain 100 PPM sodium persulfate and 10 PPM of device crystals to inhibit staph infections. The cream was applied to a "staph" infection. The infection disappeared overnight. The subject was a 24-year old female.

EXAMPLE 2

The procedures described in Example 1 were analogously followed for the yeast pathogen *Candida albicans* using strain 16464 excepting that the nutrient broth was changed to accommodate this yeast pathogen to Sabouraud dextrose broth (Difco 038217-9). It was found that 2.5 PPM of molecular crystal devices completely inhibited the growth of this gynecological yeast infection. A gynecological cream and a douche were formulated against yeasts based on the results. The douche which contained 10 PPM of crystals and 40 PPM sodium persulfate was self-administered by a woman in her thirties who had suffered an entire year from the infection and who had taken virtually every prescription medicine for the infection to no avail. After taking two 2-quart douches within 24 hours, all signs of the candida infection had disappeared and her doctor pronounced her completely cured.

EXAMPLE 3

Device crystals were administered intravenously into a person in such a manner as to give a concentration of said tetroxide crystals of 40 PPM in the bloodstream. The person was chronically ill from *Candida albicans*. The subject, a citizen and resident of Honduras, was a 33-year old female. She was completely cured within a month of taking the crystals intravenously. It should be noted that the subject was close to death as a consequence of exposure to the disease prior to the aforesaid treatment.

EXAMPLE 4

Two patients at the same clinic where Example 3 patient was treated, in San Pedro Sultas, Honduras, were suffering from acute ameobic dysentery with diarrhea and dehydration. They were similarly intravenously treated to a level of 40 PPM of the crystals. Both patients, one a 19-year old male, and the other a 62-year old male, after being given one injection started to show slight improvement after one week. After one month had elapsed, they were completely cured from their condition.

The human dosages of this and the previous example were known to be safe as they were pretested in mice by injecting them with said crystal devices.

EXAMPLE 5

Six C57BL mice were selected that were six months old. One mouse was untreated as a control. Another control mouse was treated with an intravenous injection via its tail with 0.1 ml. of tetrasilver tetroxide devices calculated to contain 40 PPM in the bloodstream of the mouse. Two more control mice were now infected with MAIDS virus designated culture LP-BM5. Two test mice were then infected with culture LP-BM5. The LP-BM5 culture infection was achieved with intra-peritoneal injections of 0.4 ml. of said viral suspension. Subsequent to these vital injections the test mice were injected intravenously with 0.1 ml. (through the tail) of the 40 PPM (0.08 mg.) tetrasilver tetroxide devices. The devices in each case were suspended in distilled water for 3 days prior to injection and conditioned with sodium acetate as the electrolyte of choice. After 4 weeks had elapsed, the untreated and device treated control mice were killed. The untreated control mouse had a spleen weight of 90 mg., and the device treated mouse that of 89 mg. Both mice were seen to be in perfect health. After 3.5 weeks had elapsed, one of the infected control mice was killed and showed signs of MAIDS infection with a spleen weight of 138 mg. After 4 weeks had elapsed, the second infected control mouse was killed. It too showed signs of MAIDS infection with a spleen weight of 158 mg. As for the test mice, the vital suspension injection was injected immediately prior to the silver device treatment. They were then killed after 4 weeks. Both mice showed no signs of MAIDS infection, and their spleens weighed 103 and 95 mg., respectively, which are normal weights for these mice, whose body weight varies between 15–30 g. and whose blood volume is approximately 2.0 ml.

EXAMPLE 6

A 29-year old male suffering from athlete's foot soaked his feet in a solution containing 100 PPM of the crystal devices. The subject was completely cured within 24 hours.

EXAMPLE 7

A 61-year old male who suffered from a toenail fungus was treated with a 25% suspension of said crystal devices. The nail fungus, which had bothered the subject for three years, was gone after a week.

While there is shown and described herein certain specific examples embodying the invention, it will be manifest to those skilled in the art that various modifications and rearrangements of the invention may be made without departing from the spirit and scope of the underlying inventive concept and that the same is not limited to the particular forms herein shown and described except insofar as indicated by the scope of the appended claims.

What is claimed is:

1. A method for curing amoebic dysentery comprising, administering crystals of tetrasilver tetroxide intravenously so as to give a concentration of crystals of 40 PPM in the bloodstream.

2. A method for treating systemic *Candida albicans;* comprising injecting tetrasilver tetroxide crystals into the blood of humans so as to give a concentration of approximately 40 PPM in the bloodstream.

3. A method for treating *Candida albicans* according to claim 2 comprising only one single administered injection.

\* \* \* \* \*